(12) United States Patent
Franzen et al.

(10) Patent No.: US 10,457,972 B2
(45) Date of Patent: Oct. 29, 2019

(54) MASS SPECTROMETRIC DETERMINATION OF MICROBIAL RESISTANCES

(71) Applicant: Bruker Daltonik GmbH, Bremen (DE)

(72) Inventors: Jochen Franzen, Bremen (DE);
Markus Kostrzewa, Lilienthal (DE);
Christoph Lange, Grasberg (DE);
Katrin Sparbier, Bremen (DE)

(*) Notice: Subject to any disclaimer, the term of this patent is extended or adjusted under 35 U.S.C. 154(b) by 1025 days.

(21) Appl. No.: 14/271,508

(22) Filed: May 7, 2014

(65) Prior Publication Data

US 2014/0335556 A1    Nov. 13, 2014

(30) Foreign Application Priority Data

May 8, 2013 (EP) .................................... 13002450

(51) Int. Cl.
*C12Q 1/04* (2006.01)
(52) U.S. Cl.
CPC ........... *C12Q 1/04* (2013.01); *G01N 2560/00* (2013.01)
(58) Field of Classification Search
CPC .............................. C12Q 1/04; G01N 2560/00
See application file for complete search history.

(56) References Cited

U.S. PATENT DOCUMENTS

| | | | | |
|---|---|---|---|---|
| 8,293,496 | B2 * | 10/2012 | Govorun | G01N 33/6851 435/32 |
| 8,580,535 | B2 * | 11/2013 | Govorun | G01N 33/6851 435/34 |
| 9,051,594 | B2 * | 6/2015 | Govorun | G01N 33/6851 |
| 2008/0044857 | A1 * | 2/2008 | Anderson | C12N 15/1065 435/71.1 |
| 2011/0300552 | A1 | 12/2011 | Demirev et al. | |
| 2014/0106396 | A1 * | 4/2014 | Govorun | C12Q 1/18 435/32 |

OTHER PUBLICATIONS

Collier et al. (2010) Analytical Chemistry 82(20): 8696-8702.*
Food and Drug Administration (Sep. 2017) Statistical Approaches to Evaluate Analytical Similarity: Guidance for Industry, pp. 1-12.*
Penny et al. (2016) Frontiers in Microbiology 7: 1-9. (Year: 2016).*
Camara et al. (2007) Analytical Bioanalytical Chemistry 389: 1633-1638. (Year: 2007).*
Welker et al. (2011) Systematic and Applied Microbiology 34: 2-11. (Year: 2011).*
Lasch et al. (2014) J Microbiol Meth 100: 58-69. (Year: 2014).*
Sparbier et al. (2013) J. Clin. Microbiol. 51(11): 3741-3748. (Year: 2013).*
Jung et al. (2014) Eur. J. Clin. Microbiol. Infect. Dis. 33: 949-955. Published online Dec. 14, 2013. (Year: 2014).*
Pittenauer et al. (2006) J. Mass Spectrometry 41: 421-447. (Year: 2006).*
Dulbecco's Modified Eagle's Medium (DME) Formulation, http://www.sigmaaldrich.com/life-science/learning-center/media-formulations/dme.html.
Ong, Shao-En, et al., A practical recipe for stable isotope labeling by amino acids in cell culture (SILAC), Nature Protocols, Jan. 11, 2007, vol. I, No. 6, pp. 2650-2660.
Harsha, H.C., et al., Quantitative proteomics using stable isotope labeling with amino acids in cell culture, Nature Protocols, Mar. 6, 2008, vol. 3, No. 3, pp. 505-516.
Demirev, Plamen A., et al., Establishing Drug Resistance in Microorganisms by Mass Spectrometry, J. Am. Soc. Mass Spectrom., Apr. 9, 2013, 24, pp. 1194-1201.
Mann, Matthias, Functional and quantitative proteomics using SILAC, Nature Reviews, J. Molecular Cell Biology, Dec. 2006, vol. 7, pp. 952-959.
Dilworth, David J., et al., QTIPS: A Novel Method of Unsupervised Determination of Isotopic Amino Acid Distribution in SILAC Experiments, J. Am. Soc. Mass Spectrom., Apr. 8, 2010, 21, 1417-1422.
Wikipedia, Growth Medium, Update of Apr. 4, 2013, https://en.wikipedia.org/w/index.php?title=Growth_medium&oldid=548660997.

* cited by examiner

*Primary Examiner* — Lisa J Hobbs
(74) *Attorney, Agent, or Firm* — Benoit & Côté Inc.

(57) ABSTRACT

The invention relates to a mass spectrometric method for determining microbial resistances to antibiotics. The invention provides specific methods comprising cultivation in synthetic media, in which several amino acids, preferably only a single amino acid, are isotopically labeled by incorporating $^{13}C$, $^{15}N$, $^{18}O$ or $^{34}S$. If several amino acids are isotopically labeled, they are labeled in such a way that they are each heavier than the corresponding unlabeled amino acids by the same integer mass difference $\Delta m$. This ensures that the mass shifts of the peaks always amount to an integer multiple of the mass difference $\Delta m$. The total mass difference can be kept relatively small by selecting suitable amino acids. A mass shift of the protein peaks in media with antibiotics indicates that the microbes are resistant. A second embodiment first produces isotopically labeled microbes, which are then tested for their resistance by cultivating them in normal media.

19 Claims, 3 Drawing Sheets

(Susceptible Germ)

(Resistant Germ)

Top: Normal medium
Center: Isotope-labeled medium with antibiotic
Bottom: Isotope-labeled medium without antibiotic

MASS SPECTROMETRIC DETERMINATION OF MICROBIAL RESISTANCES

BACKGROUND OF THE INVENTION

Field of the Invention

The invention relates to a mass spectrometric method of determining microbial resistances to antibiotics using isotopically labeled nutrient components.

Description of the Related Art

Instead of the statutory "unified atomic mass unit" (u), this document uses the unit "dalton" (Da), which was added in the last (eighth) edition of the document "The International System of Units (SI)" of the "Bureau International des Poids et Mesures" in 2006 on an equal footing with the atomic mass unit; as is noted there, this was done primarily in order to be able to use the units kilodalton, millidalton and similar.

For reasons of simplicity, only the term "proteins" is used in this document, although in the mass range considered here it would often be better to call the proteins "peptides". The transition from the lighter peptides to the heavier proteins is fluid, however, and not precisely defined.

The term "antibiotic" here covers pharmacologically active substances for the treatment of bacterial infectious diseases and other antibacterial substances, for the purpose of disinfection, for example.

The successes of penicillin, but also the appearance of the first resistances, led researchers to search for and discover many more antibiotics. Ever since penicillin was used as the first pharmacologically active substance, bacterial strains have increasingly developed various types of resistance, i.e. they have acquired characteristics which allow them to weaken the effect of antibiotic substances or to neutralize it completely. Resistances are now widespread: in the USA, around 70% of the infectious germs acquired in hospitals are resistant to at least one antibiotic. Patients are often infected with bacterial strains which are resistant to several antibiotics (multi-resistance). The so-called problematic germs are mainly methicillin-resistant *Staphylococcus aureus* (MRSA), *Pseudomonas* spec., *Escherichia coli* with ESBL resistance and *Mycobacterium tuberculosis*. The CDC (Center for Disease Control and Prevention) estimates that two million infections were acquired in hospitals in the USA in 2004, with around 90,000 deaths.

The reasons for the increase in resistances are manifold: irresponsible prescription of antibiotics, even when not necessary; courses of treatment which are irresponsibly broken off; irresponsible, often purely preventative usage in agriculture and animal husbandry. All these types of behavior help to select and spread resistant bacterial strains, as opposed to non-resistant bacterial strains.

The success of a therapy for bacterial infections, which can be life-threatening in acute situations, such as sepsis, or as a secondary infection during an existing primary illness (or primary infection), often depends on the first administration of an antibiotic being effective. Targeted administration requires not only that the pathogen is identified as quickly and correctly as possible, but also that its resistance to different antibiotics is determined quickly.

In routine microbiological work nowadays, the resistance of microbes is determined by culturing microbes from a sample under investigation in vitro on nutrient media (e.g., agar plates) or in nutrient media (e.g., culture broths), to which an antibiotic is added in each case. Whether the microbes multiply under the influence of the antibiotic, i.e., are resistant to the antibiotic, is determined visually by eye or in an automated process using optical devices. The routine method based on an optical evaluation allows a simple determination of the resistance, but it is time-consuming because the cultivation has to be carried out until an optically discernible effect is achieved. This method usually takes 24 to 48 hours. An advantage of this routine method consists in the fact that the efficacy or inefficacy of an antibiotic against the microbes of a sample is measured directly (it is a "functional test").

The usual procedure is to test cultures with graduated concentrations of the antibiotic in order to determine the "minimum inhibitory concentration" (MIC). The minimum inhibitory concentration designates the lowest concentration of a substance at which the multiplication of a microorganism can no longer be perceived visually. The usual practice is to determine the MIC, but some antibiotics can also be characterized via the "minimum bactericidal concentration" (MBC), where 99.9% of the germs are killed within a fixed period of time. While the MIC can be determined, in principle, for every antibiotic, the MBC only makes sense for those antibiotics which can develop not only an inhibitory, but also a bactericidal effect. These are aminoglycosides, gyrase inhibitors and penicillins, for example. On the basis of the resistance determined, the detected germs are termed S—sensitive, I—intermediate or R—resistant.

In addition to culturing in the presence of antibiotics, there are also genetic methods to determine resistances. Here, a resistance is determined by detecting known resistance genes in the genome of the pathogen in question. An advantage of the genetic methods consists in the fact that the resistance genes can be amplified by techniques such as polymerase chain reaction (PCR), and thus the time needed for the analysis is no longer determined by the growth rate of the bacteria. The disadvantages are that they are more expensive than routine methods and are not functional tests. A resistance gene may be present, but not be expressed, which means the bacterial strain under investigation is not resistant, but the method detects it as being resistant.

Many species of microorganism, particularly bacteria and unicellular fungi such as yeasts, can be identified by mass spectrometry nowadays—quickly and with low error rates. The term "identification" here means taxonomic classification, i.e. the determination of family, genus and species. In routine laboratory work, the identification is achieved by means of a similarity analysis between a MALDI mass spectrum (MALDI=Matrix Assisted Laser Desorption/Ionization) of the sample under investigation and MALDI reference spectra of known microorganisms. In the similarity analysis, each reference spectrum is assigned a classification number, which is a measure of the agreement between the corresponding reference spectrum and the mass spectrum of the sample. If the similarity values exceed certain threshold values, family, genus, species and even strain can be identified. This method for identifying microorganisms has proven to be extraordinarily successful, both in large-scale studies and in the daily routine in many microbiological laboratories. Depending on the instrument, 48 to 384 microbial samples can be determined at the same time. After cultivation of a colony, it takes only minutes to identification. It is thus a fast and low-cost method having very low error rates, far lower than conventional microbiological identification methods. Recent studies confirm that this mass spectrometric identification method is more reliable at providing correct results than DNA analysis, which has been deemed to be the "gold standard" to date. There are meanwhile mass spectrometers, associated evaluation programs, and libraries of reference spectra on the market which are certified as IVD products for medical diagnostics in accordance with the German Medical Devices Act (MPG) and other, national and international regulations and guidelines.

Attempts have been made to extend the mass spectrometric identification of microorganisms to a mass spectrometric determination of their resistances. Unfortunately, determining resistances directly from a mass spectrum has so far only proved possible in rare exceptional cases, even though the resistances should also be detectable from the presence of new or modified proteins.

The patent specification DE 10 2006 021 493 B4 (V. M. Govorun and J. Franzen, 2006, corresponding to GB 2438066 B, U.S. Pat. No. 8,293,496 B2; called "Govorun" in the following) discloses mass spectrometric methods for determining the resistance of bacteria, in which protein profiles of the bacteria are measured by mass spectrometry after cultivation with and without added antibiotics and compared. As the patent specification explains, the resistance can, for example, be determined by the fact that the microbes continue to live and take up nutrient from the medium even in the presence of antibiotics. If the medium contains isotopically labeled nutrient components, the resulting change in the mass spectra indicates the resistance. Non-resistant microbes, on the other hand, suffer a growth inhibition or a structural destruction and no longer take up such nutrient components. Like the routine method described above, Govorun's method is a functional test, but is faster at providing measurable information than the standard optical methods.

An embodiment of the Govorun method is described in the article "Establishing Drug Resistance in Microorganisms by Mass Spectrometry", (P. A. Demirev et al.; J. Am. Soc. Mass Spectrom. (2013)). Microbes are cultivated, with the addition of antibiotics, in a medium in which all $^{12}$C atoms have been replaced by $^{13}$C. The possible shifts of mass spectrometric peaks (mass signals), which might occur in the mass spectra of the microbes from these cultures compared to the usual reference spectra, are calculated in advance, at least approximately, by means of four different methods. In the simplest method, an approximate advance calculation uses the average content of C atoms for proteins of a given mass; more complicated methods are directed to a de-novo sequencing by tandem MS or to an identification with the aid of protein databases. These shifted peaks should only be found where there is a resistance, because only resistant microbes can grow when antibiotics are present. This method is decidedly expensive, however, because it uses a completely isotope-labeled medium; in addition, the prediction of the peak shifts is either imprecise or elaborate.

In the patent application WO 2011/152899 A1 (P. A. Demirev et al.), as stated in the abstract, mass spectra of microbes, or of isolated biomarkers from microbes which have grown in an isotope-labeled medium with an antibiotic, are compared with mass spectra from microbes or biomarkers from microbes which have grown in normal media without antibiotic. The resistance is determined by predicting and detecting a characteristic mass shift, which indicates that the microbe grows in the presence of an antibiotic and takes up isotopically labeled material in one or more biomarkers, causing the mass shift.

There is an ongoing effort to provide a mass spectrometric method with which the resistance of microbes to one or more antibiotics can be determined relatively quickly (preferably in less than eight hours), with certainty and, most importantly, at low cost also. It should preferably be possible to carry out the method in a routine mass spectrometer, which is also used for identifications.

SUMMARY OF THE INVENTION

The present invention provides a first method for the mass spectrometric determination of microbial resistance, where the microbes from a sample under investigation are cultivated in a first and a second culture in which a medium with isotope-labeled nutrient components is used, the first culture with the addition of an antibiotic and the second culture without the addition of an antibiotic. Afterwards, mass spectra of the microbes from both cultures are acquired and compared. The medium here is a synthetic medium which contains proteinogenic amino acids, and at least one of the amino acids is isotopically labeled, and all the isotopically labeled amino acids have the same integer mass difference $\Delta m$ in relation to the corresponding unlabeled amino acids. The term "amino acid" is used below synonymously with type of amino acid.

The synthetic medium used in the method preferably contains only one isotopically labeled amino acid, which amounts to less than five percent, in particular less than one percent, in ribosomal proteins of the microbes. The synthetic medium used in the method can also contain more than one isotopically labeled amino acid, amounting to less than ten percent in total, in particular less than five percent, in ribosomal proteins of the microbes. Furthermore, in addition to the amino acids, the synthetic medium preferably contains carbohydrates, vitamins and minerals.

The microbes of the sample under investigation can additionally be cultivated in a third culture in the synthetic medium, which contains only unlabeled amino acids and no antibiotic. A mass spectrum of the microbes from the third culture is acquired and compared with the mass spectrum of the first culture. The microbes are identified as resistant if the mass spectrum of the first culture (with antibiotic/with at least one isotopically labeled amino acid) has greater similarity to the mass spectrum of the second culture (without antibiotic/with at least one isotopically labeled amino acid) than to the mass spectrum of the third culture. The similarity between the mass spectra can be determined by means of various mathematical-statistical analytical methods, such as a cross-correlation, ANN (Artificial Neural Network Analysis), PCA (Principal Component Analysis), PLS-DA (Partial Least-Square Discriminant Analysis), SVM (Support Vector Machines), hierarchical cluster analyses or other supervised or un-supervised classification techniques. If more than the three mass spectra are required for a mathematical-statistical analytical method, several repeat spectra can be acquired from microbes of the three cultures.

In order to test the resistance to several antibiotics, the first method requires several isotope-labeled cultures to be prepared with several antibiotics, where necessary even with different concentration levels of the antibiotics in each case. Since the use of such a large number of cultures with an isotope-labeled medium (each with at least one isotope-labeled amino acid) is expensive, a second method according to the invention is proposed, which takes slightly longer, but is cheaper.

The second method for the mass spectrometric determination of microbial resistance according to the invention comprises the following steps: (a) cultivation of the microbes in a synthetic medium in which at least one of the amino acids is isotopically labeled and all the isotopically labeled amino acids in the medium have the same integer mass difference $\Delta m$ in relation to the corresponding unlabeled amino acids, (b) cultivation of the microbes cultivated in step (a) in a first and a second culture with a normal medium without isotopically labeled nutrient components, with and without the addition of an antibiotic respectively, and (c) determination of resistance to the antibiotic by acquiring and comparing mass spectra of the microbes from the first and second cultures.

The second method is essentially based on the fact that microbes are at first sufficiently generated in the first step using a first culture with a medium comprising at least one isotope-labeled amino acid, carbohydrates, vitamins and minerals wherein the relevant amino acids are almost completely replaced by the isotopically labeled amino acids in the microbes. In the second step, these isotopically labeled microbes are then cultivated in normal media which are not isotope-labeled, and which are both inexpensive and can provide optimum growth conditions. The isotopically labeled microbes can now be cultivated in a low-cost normal medium without antibiotics and simultaneously in several low-cost normal media with different antibiotics, each at several levels of concentration if required. Resistant microbes now form new proteins with unlabeled amino acids, while the proteins with isotopically labeled amino acids are diluted more and more; non-resistant microbes with growth retardation keep most of their proteins with isotopically labeled amino acids.

In the second method also, it is advantageous to use only one or a small number of less frequently occurring amino acids, or occurring with average frequency, in the isotopically labeled form. The synthetic medium used in the first cultivation step (a) preferably comprises only one isotopically labeled amino acid, which amounts to less than five percent, in particular less than one percent, in ribosomal proteins of the microbes. The synthetic medium can also comprise more than one isotopically labeled amino acid, amounting to less than ten percent in total, in particular less than five percent, in ribosomal proteins of the microbes.

Similar to the first method, a third mass spectrum can be acquired from the microbes cultivated in step a) and compared with the mass spectrum of the first culture. The microbes are identified as resistant if the mass spectrum of the first culture (with antibiotic) has greater similarity to the mass spectrum of the second culture (without antibiotic) than to the third mass spectrum. As has already been described above, the similarity between the mass spectra can be determined using various mathematical-statistical analytical methods.

The invention provides specific embodiments of the Govorun method with isotopically labeled nutrient components. In contrast to the embodiment from Demirev et al., a synthetic medium is used in which only a few amino acids, preferably only a single one, are isotopically labeled by incorporating $^{13}C$, $^{15}N$, $^{18}O$ or $^{34}S$. If more than one amino acid is isotopically labeled, they are labeled in such a way that they are all heavier than the corresponding unlabeled amino acids by the same integer mass difference $\Delta m$. Thus, instead of being forced to make complicated advance calculations of the shifts of certain "biomarkers" (or even MS/MS measurements and identification of these biomarkers), as is the case in Demirev et al., the present invention uses a medium which automatically leads to peak shifts of $n \times \Delta m$ for all proteins which contain these isotopically labeled amino acids, wherein n represents the number of isotopically labeled amino acids in the protein in each case. The mass differences $\Delta m$ between the isotopically labeled amino acids and the corresponding unlabeled amino acids should be between 6 and 12 daltons, preferably at 8 to 10 daltons.

Demirev et al. determine the resistance of a microbe by detecting shifted peaks. In our experiments, however, it has been found that non-resistant microbes in an isotope-labeled medium can also take up a certain amount of isotopically labeled nutrient components, even in the presence of antibiotics, before complete growth retardation or structural destruction occurs. And even after hours of cultivation, resistant microbes can still contain a proportion of unlabeled amino acids, which would mathematically not be expected, given the doubling time.

In both methods according to the invention, the resistance of the microbes can be determined from the ratios of the intensities of shifted and un-shifted peaks (mass signals) of the same proteins in each case. The condition for this approach is that the shifted peaks can be individually and unequivocally assigned to the un-shifted ones, and that possible overlap with peaks of other proteins can be detected and taken into account. It is advantageous here to find as many shift pairs as possible. In addition to the ratios of the intensities, it is also possible to use the relative or absolute differences in the ratios of the peak intensities to determine the resistances.

Between 60 and 85 percent of the proteins measured in mass spectra belong to the ribosomal proteins. The amino acids are not equally distributed in these ribosomal proteins—as is also the case with other proteins—but there are rarer amino acids at less than five percent and more frequently occurring amino acids at more than five percent (if they were equally distributed, all 20 amino acids would occur with a frequency of 5%). Amino acids which occur frequently can quite easily occur around 20 to 40 times in a single protein in the upper measured mass range—the mass spectrum from three up to around 15 kilodaltons is usually measured—while rarer amino acids only occur up to around 4 to 6 times. The peak shifts are therefore much easier to detect individually for rarer amino acids, or those with average occurrence, than for amino acids occurring with very high frequency. Since the calculation of the intensity ratios requires that the peak pairs which correspond to each other must be able to be located individually, it is better to label one or more of the rarer amino acids or those which occur with average frequency.

In both methods according to the invention, the microbes of a sample under investigation can be cultivated in cultures to which an antibiotic has been added at different levels of concentration in order to determine, or at least estimate, the MIC value of the antibiotic with a quantitative evaluation of the mass spectra at different concentrations. In the second method, at step b), several cultivations can be carried out with the normal medium with the addition of different antibiotics and/or different concentrations in each case.

The synthetic medium used in the methods according to the invention essentially does not comprise the unlabeled amino acid corresponding to an isotopically labeled amino acid. The term "essentially" means that the ratio of the corresponding unlabeled amino acid to the isotopically labeled amino acid is less than twenty percent, preferably less than 5 percent, in particular less than one percent, or that the corresponding unlabeled amino acid is not present at all in the medium. Furthermore, the synthetic medium can comprise a mixture of different antibiotics instead of a single antibiotic. The cultivation steps of the methods according to the invention preferably take place in a compact volume of liquid (e.g., in a centrifuge tube or the wells on a microtiter plate), but can also take place in appropriate agar plates in Petri dishes.

The invention, furthermore, provides a medium according to the invention for the cultivation of microbes, which is a synthetic medium with proteinogenic amino acids, at least one of which is isotopically labeled. Here the corresponding unlabeled amino acid is essentially completely replaced by the isotopically labeled amino acid, i.e. that the ratio of the corresponding unlabeled amino acid to the isotopically labeled amino acid amounts to less than twenty percent, preferably to less than 5 percent, in particular to less than one percent, or that the corresponding unlabeled amino acid is not present in the medium at all. The synthetic medium is preferably Eagle's minimal essential medium (EMEM) or Dulbecco's modified Eagle's medium (DMEM), in which at least one of the amino acids has been replaced by a corresponding isotopically labeled amino acid. The synthetic medium has, furthermore, a NaCl concentration of more than 6.4 g/l and/or contains Fe(II)SO$_4$.

The methods and media according to the invention can also be used to determine a resistance of unicellular fungi (yeasts) to an antimycotic or a mixture of antimycotics.

DETAILED DESCRIPTION

Figure 1:
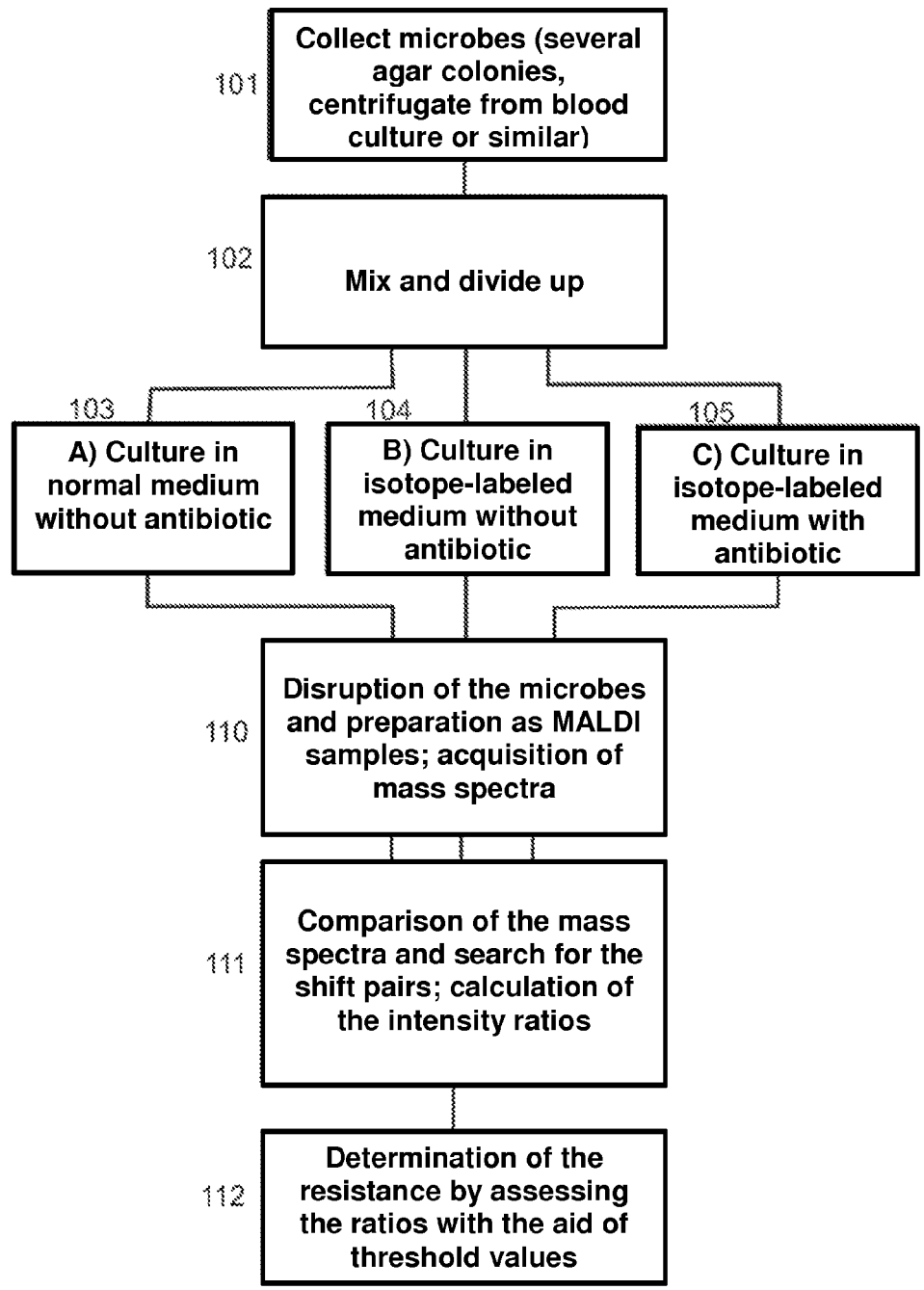
FIG. 1 shows an example of a flow diagram for determining the resistance according to a first embodiment of the invention.

All the embodiments listed here presuppose that the microbes whose resistance is to be determined are present in sufficient quantities and in a sufficiently pure form. They can be present in the form of colonies on an agar, or as microbes from a blood culture, for example. With agar cultures, it is common practice to use microbes from not just one colony for the testing, but to subject the microbes from at least five colonies together to the testing in order to also identify the presence of a resistant microbe among non-resistant microbes of the same species, where applicable. A trained and experienced assistant is generally able to recognize colonies of the same microbes and to harvest them. They must then be mixed and divided up for the cultures. For microbes from blood cultures, in particular from positive blood cultures, a mixture of the different species of microbes is also probable.

As has already been noted above, the method provides particularly advantageous embodiments of the Govorun method with isotopically labeled nutrient components. The method by Demirev et al. uses a medium which is completely $^{13}$C labeled and thus expensive, and requires complicated methods to determine the shift of individual biomarker peaks in advance. In contrast to the above, the present invention uses a synthetic medium in which one or a small number of amino acids are isotopically labeled by $^{13}$C, $^{15}$N, $^{18}$O and/or $^{34}$S, and in which these isotopically labeled amino acids are all heavier than the corresponding unlabeled amino acids by the same fixed mass difference $\Delta m$. In one embodiment, it is even the case that only one single amino acid is isotopically labeled. Thereby, it is achieved that the mass difference $\Delta m$ of the peak pairs in the mass spectra with and without take up of the isotopically labeled nutrient components is always an integer multiple of the mass difference $\Delta m$ between the isotopically labeled amino acids and the unlabeled amino acids. (Isotope labeling with $^2$D is avoided here because this is too easily transferred to other molecules by H/D exchange. Isotope labeling with phosphorus, also mentioned by Demirev et al., is used less preferably here because there is only one stable phosphorus isotope $^{31}$P.)

MALDI time-of-flight mass spectrometers in linear mode, i.e., without using a reflector, are the main instruments currently used for the identification of microbes. In order to achieve a high sensitivity, the laser energy for the ionization is chosen to be very high, whereby most of the ions produced are highly excited so that they decompose during the time of flight. In order to also measure the decomposed particles, whether neutral or still charged, and whether changed in mass or not, in the mass spectrum, they are measured without reflection at the end of the flight path. A secondary electron multiplier can also measure the neutral particles. However, the mass resolution suffers because the decomposition releases small amounts of energy, which are passed on to the decomposition products as kinetic energy, and thus their flight speed is statistically slightly diminished or increased. The isotope distributions, which can be resolved efficiently into individual peaks up to very high masses using good time-of-flight mass spectrometers with reflectors, form only a single, relatively broad peak here.

Due to this low mass resolving power, the mass difference in the lower mass range of the measured mass spectrum, i.e., at around three kilodaltons, must be at least $\Delta m=6$ to be detectable. Mass differences of the amino acids with and without isotopic labeling of $\Delta m=6$ to 12 daltons, preferably $\Delta m=8$ to 10 daltons, are favorable; it is then possible to detect peak shifts which originate only from one isotopically labeled amino acid. In the upper mass range, where an even lower mass resolution prevails, several isotopically labeled amino acids are usually present, so that a multiple of the minimum mass difference $\Delta m$ is predominately present, and the peak shift can be resolved accordingly.

It should be noted here that the majority of all the peaks in the mass spectrum are shifted if there is a resistance. The mass spectrum predominantly comprises mass signals from proteins (protein peaks). The absence of a peak shift only occurs in the rare cases where a protein does not contain the amino acid which is present in the medium in isotopically labeled form. A small number of mass signals originating from cell components which contain no amino acids are not shifted either. The larger the mass, the higher the probability that a shift of a peak has to occur, because at larger mass the peaks predominantly originate only from proteins (or protein derivatives) and these proteins very probably comprise the labeled amino acids due to their size.

It has been found experimentally that, fortunately, with most microbes no proteins which carry a mixture of unlabeled and labeled amino acids of the same type are formed in measurable quantities. This indicates that the measured proteins are newly built up to a large extent from isotopically labeled amino acids which are contained in the nutrient components taken up, and only rarely from amino acids which are newly synthesized in the microbes from glucose (bacteria are quite able to newly form amino acids from hydrocarbons. Specially cultivated bacteria of the *Coryne-*

*bacterium glutamicum* species are even used to produce several hundred thousand tonnes of L-lysine annually, at a value of more than two billion euros, with molasses serving as a nutrient).

Since mixed forms occur only rarely, measurable peak shifts are almost exclusively by a fixed value of n×Δm, with a fixed number n. This results in the formation of predominantly cleanly separated peak pairs.

It has also been found experimentally that when the method is applied in an optimum way, a relatively short cultivation period of only around three hours is sufficient to determine the resistance. The method is thus extremely fast; within three to four hours after the identification of a microbe species it is possible to determine whether the microbes are resistant.

It is one of the special findings on which this invention is based that, for short cultivation periods in particular, it is very important to be able to individually detect peak pairs, which each comprise a non-shifted and a shifted peak. It was found namely that non-resistant microbes in the isotope-labeled medium can also take up a certain amount of isotopically labeled nutrient components, even in the presence of antibiotics, before complete growth retardation or structural destruction occurs. Furthermore, even after hours of cultivation, resistant microbes can still contain by an unresolved way relatively large amounts of proteins made up of completely unlabeled amino acids, larger amounts than would mathematically be expected from the knowledge of the doubling time. It is therefore most preferable to determine the resistance from the ratios of the intensities of the isotopically shifted peaks to the corresponding un-shifted peaks. It is particularly favorable to calculate many ratios from the intensities of the isotopically shifted peaks in relation to the corresponding un-shifted peaks, and to derive the resistance from this with increased certainty. This approach requires that it must be possible to assign the shifted peaks individually and unequivocally to the un-shifted ones. It is, furthermore, important to recognize potential overlaps of the shifted peaks with peaks of other proteins which can occur in the non-isotope-labeled spectrum and to exclude any such overlapped peaks from the calculation, or to take the overlap into account in the calculations.

It is important for the individual detectability of the peak pairs that they are not too far apart. It is understandably easier to only have to look for the associated peak in around 5 places rather than in 20 to 40 places, which are correspondingly several hundred daltons away in the mass spectrum and possibly comprise numerous other shifted and un-shifted peaks in between. To avoid large mass differences, the isotopic labeling must not be extended to large numbers of amino acids, nor must the labeled amino acids occur in large numbers in a protein.

It is known that between 60 and 85 percent of the proteins measured in mass spectra belong to the ribosomal proteins. If all the amino acids were distributed equally, a protein would comprise five percent of each of the 20 amino acids. The amino acids are not distributed equally in these ribosomal proteins, however—in fact, the distribution is more disparate than in other proteins—but there are rarer amino acids at less than five percent, and more frequently occurring amino acids at more than five percent. Very frequently occurring amino acids (such as lysine) can quite easily amount to 15 to 30 percent of all the amino acids in ribosomal proteins. These can quite easily occur around 20 to 40 times in a protein in the upper measured mass range—the mass spectrum is usually limited to the range from three up to around 15 kilodaltons—while rarer amino acids, or those with average frequency, occur only around 3 to 6 times. At around 15 kilodaltons, the proteins have around 120 to 140 amino acids; in the mass range around 3,000 daltons, only 25 to 30 amino acids. An amino acid with an average frequency of five percent therefore occurs in the lower mass range only once on average, in the upper mass range six to seven times. For a rarer amino acid, or one with average frequency, the peak shifts are thus much smaller and very much easier to find individually than for amino acids which occur with high frequency. Since the calculation of the intensity ratios, which has proved to be the preferred form of evaluation, requires that it must be possible to individually detect the corresponding peaks of peak pairs, it is preferable to label a rarer amino acid, or one which occurs with average frequency, leucine for example.

It can, furthermore, be advantageous to use more than one amino acid with isotopic labeling, for example two or three, up to a maximum of four. These can be selected, for example, so that in total they amount to less than five to ten percent of all the amino acids of the ribosomal proteins, but that each ribosomal protein comprises at least one of these amino acids, if possible. For the shift to be easily detectable, it is again necessary for all the isotopically labeled amino acids to have the same mass difference Δm in relation to the corresponding unlabeled amino acids. This means that practically all the peaks, if they actually originate from proteins, are shifted if a resistance is present.

As has already been noted above, a preferred way of determining the resistances is to calculate the intensity ratios for the individual peak pairs of the shift. The intensity ratios can be compared individually with threshold values gained from experience, or can first be averaged in order to compare the average with a threshold value from experience. When the ratio of the intensity of the shifted and the un-shifted peak has been formed, ratios above the threshold value indicate a resistance. Comparing the individual ratios has the advantage that outliers can be recognized and that it is even possible to use mass-dependent threshold values.

It should be noted that, in addition to the ratios of the intensities of the shifted and un-shifted peaks, it is also possible to use the relative or absolute differences of the ratios of the peak intensities to determine the resistances.

Computational methods for the determination of resistances which are not based on the individual recognition of the peak pairs have also been tested. The shift of the centroid of the mass spectrum can be calculated with known algorithms, for example. This shift of the centroid should be a measure for the resistance, especially if, in contrast to the above-stated recommendations, very frequently occurring amino acids, or even several frequently occurring amino acids, are isotopically labeled. It has been found, however, that this computational method does not always indicate the resistance with the desired degree of certainty. Since only a section of the mass spectrum (for example from three to fifteen kilodaltons) is ever measured, one can definitely expect that shifted peaks will migrate into the mass range at the lower limit, and migrate out of it at the upper limit, which falsifies the calculation of the centroid.

In order to determine or estimate the MIC values (minimum inhibitory concentrations) of the antibiotics, cultures with added antibiotic can be used at various concentration levels. The conventional MIC values of the different antibiotics for certain microbes are well known; there are occasionally large and surprising deviations, however. In order to roughly check these MIC values, antibiotics at various concentration levels can be added to different cultures, corresponding to the concentrations 1*MIC, 10*MIC and 100*MIC of the MIC values known to date, for example. Experience has shown that the method described above just fails to detect the effect of the 1*MIC concentration, but detects the effect of 10*MIC clearly, and the effect of 100*MIC very strongly. The effect can be seen from the values of the individual or averaged intensity ratios, for example. If the method is carried out without different levels of concentration, an antibiotic concentration of 10*MIC has proved to be particularly advantageous for the methods according to the invention.

The sequence of a first preferred embodiment for determining resistances is shown in the diagram of FIG. 1. The microbes are first collected (101), mixed and divided up for different types of culture (102). They are then cultivated in one medium without isotopic labeling and without antibiotics (103), in one medium with isotopic labeling but without antibiotics (104) and in one medium with isotopic labeling and with antibiotic (105). The microbes from the three cultures are then processed to become MALDI samples, and mass spectra are acquired (110). The shift pairs are searched for, and the ratios of the intensities of the respective peak partners are formed (111). The resistance is determined by comparing the ratios with threshold values, which are present as empirical values (112).

Figures 3A, 3B:
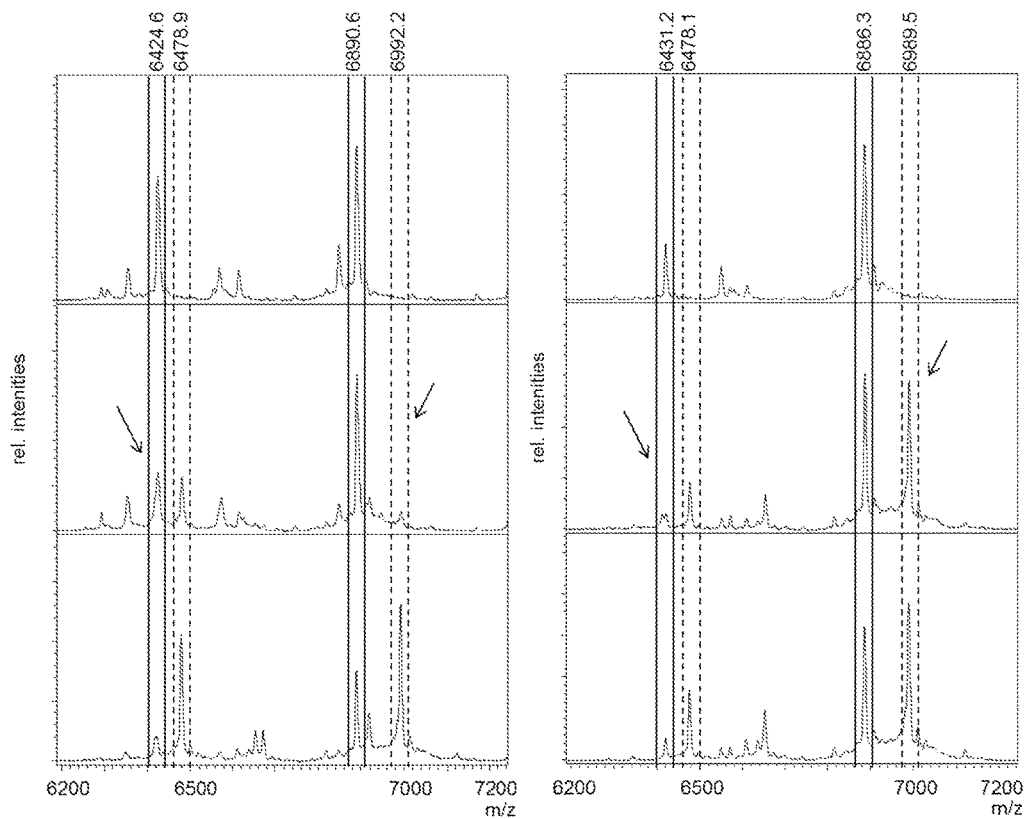
FIG. 3A shows sections from three mass spectra for a susceptible bacterium, with the top spectrum being after growth with a normal medium, the center spectrum being after growth with an isotope-labeled medium with an antibiotic, and the bottom spectrum being after growth with an isotope-labeled medium without an antibiotic.
FIG. 3B shows sections from three mass spectra for a resistant bacterium, with the top spectrum being after growth with a normal medium, the center spectrum being after growth with an isotope-labeled medium with an antibiotic, and the bottom spectrum being after growth with an isotope-labeled medium without an antibiotic.

Shown in FIGS. 3A and 3B are sections from three mass spectra acquired using a method like that shown in FIG. 1. The arrangement of each figure is similar, but FIG. 3A shows the mass spectra for a susceptible germ, while FIG. 3B shows the mass spectra for a resistant germ. At the top of each figure is a mass spectrum of the germ in question grown in a normal medium. In the middle of each figure is a mass spectrum of the germ in question grown in an isotope-labeled medium with an antibiotic. Finally, at the bottom of each figure is a mass spectrum of the germ in question grown in an isotope-labeled medium without an antibiotic. Arranged in this format, it is readily apparent how each of the germs grows in a normal medium, and how each grows in an isotope-labeled medium with and without an antibiotic. Moreover, a comparison of the two figures shows how differently a susceptible bacterium and a resistant bacterium respond to the various growth conditions.

To test the resistance to several antibiotics according to this embodiment of the invention, several cultures with several antibiotics must be prepared, where necessary even with different concentration levels of the antibiotics in each case. The consumption of an isotope-labeled medium is expensive for such a large number of cultures (with at least one isotope-labeled amino acid for each case). A further, modified embodiment is therefore proposed here, which takes slightly longer, but is far cheaper, especially if resistance to several antibiotics is to be tested. A decision can be made on an individual basis as to whether to utilize the time saving of the embodiment described above or the cost benefit of the embodiment now described. It should be noted here that the time and cost for the mass spectrometric measurement and determination are hardly ever of any consequence compared to the time needed for the cultivation steps of the different embodiments and the cost of the media. The mass-spectrometric measurement takes only minutes.

A second preferred embodiment comprises that, in a first step (a), sufficient microbes are generated in a first culture using a medium with a small number of up to four, but preferably fewer, isotopically labeled amino acids wherein the relevant amino acids are almost entirely present as isotopically labeled amino acids in the medium. The isotopically labeled amino acids should belong to the rarer amino acids, or to those which occur with average frequency, and amount in total to only around five to a maximum of ten percent of all amino acids in ribosomal proteins. Here too, the mass difference Δm between isotopically labeled and unlabeled amino acids should be the same for all the amino acids used. It is advantageous for this embodiment to use a starting quantity of microbes as large as possible (i.e., as many colonies as possible) in order to manage with a cultivation time of around four hours. It is possible here to again use a mixture of proteinogenic amino acids, carbohydrates such as glucose, and essential vitamins and minerals. The mixture must be adjusted to provide the best possible microbe growth.

In the second step (b) of this embodiment, the isotopically labeled microbes are then cultivated in low-cost normal media, which at the same time provide optimum growth conditions. The isotopically labeled microbes can now be simultaneously cultivated in a normal medium without antibiotics and in several normal media with antibiotics, if required at several levels of concentration in each case. If a normal medium without antibiotics and normal media with four antibiotics, each at three concentrations, are used, 13 cultures must be prepared at the same time. Resistant microbes form new proteins with unlabeled amino acids through divisions and growth, whereby the isotopically labeled amino acids are diluted more and more in few generations; non-resistant microbes without substantial growth keep most of their proteins with isotopically labeled amino acids. Here, it is also favorable to be able to easily identify the peak pairs individually by isotope labeling of only one amino acid, or a few, which occur less frequently or with average frequency, and to be able to calculate the relevant ratios. After around three hours, the cultivation results, in a third step (c), in mass spectra which indicate the resistances with certainty. Depending on where exactly in the cell the antibiotic acts, this time can also be shorter, e.g., for aminoglycosides, which intervene directly in the protein synthesis.

The type of evaluation to determine the resistances can be analogous to the evaluation used in the first embodiment; it must be noted, however, that the mass shift of the peaks is now toward lower masses.

Figure 2:
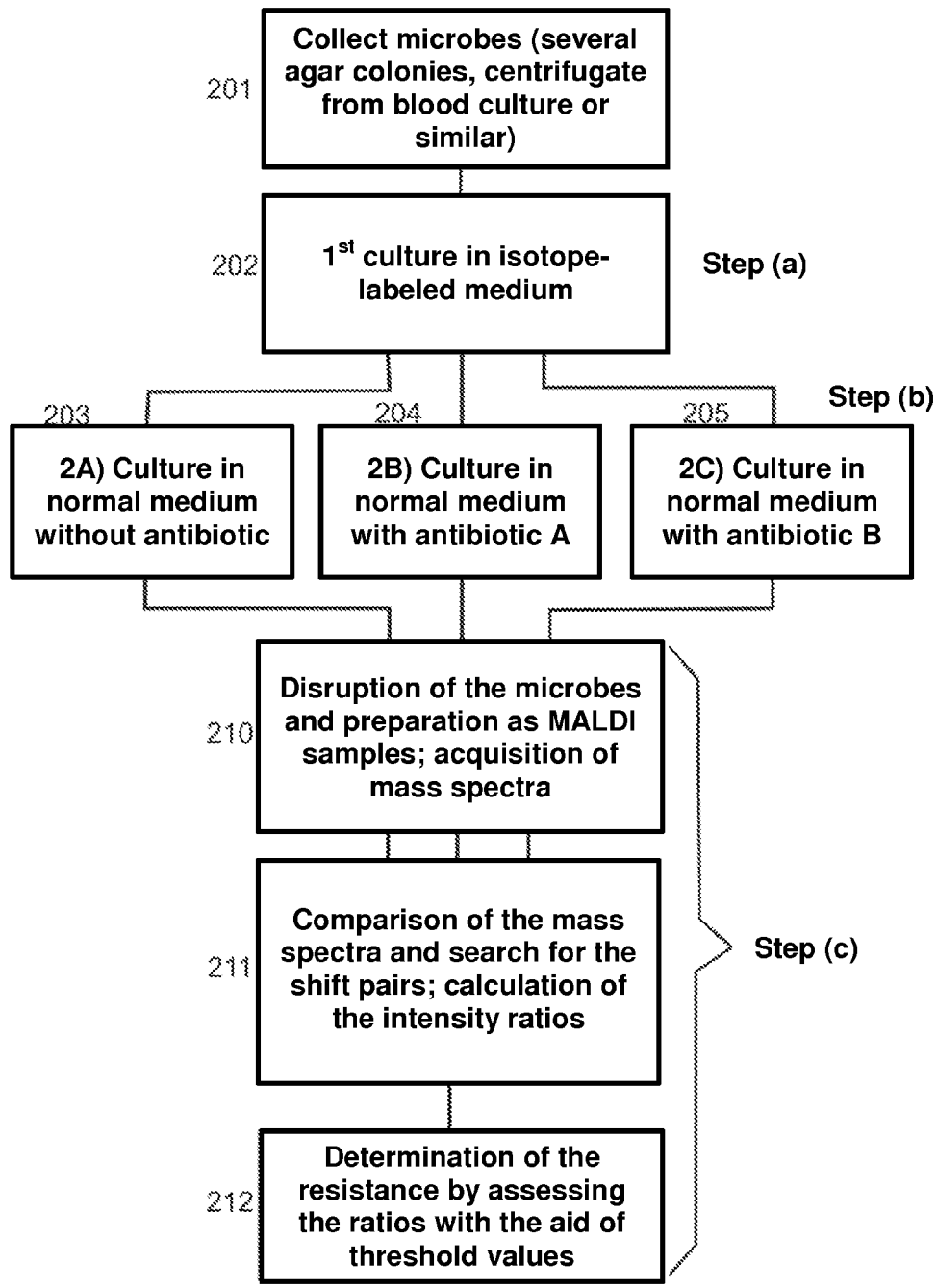
FIG. 2 shows an example of a flow diagram according to a second embodiment.

The sequence of this second embodiment is shown in the diagram in FIG. 2. At first, microbes are again collected (201). These microbes are then cultivated, in a first step (a), in a first medium with several isotopically labeled amino acids (202) to a point where they now all contain practically only these amino acids in isotopically labeled form, and no longer in their unlabeled form. In step (b), the isotopically labeled microbes are now cultivated further in several normal media: in one medium without antibiotic (203), in further media with antibiotic A (204), antibiotic B (205), etc. In step (c), mass spectra of the microbes from the various cultures are acquired (210), the ratios of the intensities of the peak pairs are formed (211), and the resistance is determined by comparing the ratios with threshold values (212).

In both embodiments, the cultivation can be carried out in centrifuge tubes (for example Eppendorf tubes) or in filter plates (for example Acropep 96-well filter plates) in each case. The further steps in processing the microbes for measurement as MALDI samples are known to those skilled in the art (MALDI=ionization by matrix-assisted laser desorption).

So far everything has been tailored to ionization by MALDI in a MALDI time-of-flight mass spectrometer. MALDI has the great advantage that the molecular ions formed are predominantly singly charged. This makes the structure of the mass spectra simple, and it is easy to find the peak shifts. But this does not mean that it is not possible to use other types of ionization. However, the spray-based methods such as ESI (electrospray ionization) or DESI (direct surface ionization of solid samples by electrospray ionization) have the disadvantage that they form too many multiply charged ions, which overload the mass spectra. There are also other ionization methods which produce predominantly singly charged ions, however, for example chemical ionization (CI). Chemical ionization can be used in conjunction with neutral spray methods, but also with laser ablation of solid samples and in conjunction with an OTOF (time-of-flight mass spectrometer with orthogonal ion injection). The mass spectra thus obtained provide extremely high mass resolution with high sensitivity (see J. Franzen and K. Michelmann, DE 10 2005 044 307 B4, for example). It is, of course, also possible to use other types of mass spectrometer if they provide the preferred mass range for spectral measurement. It is also possible to separate the microbe proteins in advance using separation methods such as HPLC or electrophoresis, but this does not appear to be very advantageous because the analysis takes much longer.

The basis of the culture medium can be DMEM (Dulbecco's modified Eagle's medium), for example, which is also available in forms where individual (or several) amino acids are missing so that isotopically labeled amino acids can be added. DMEM has been developed for cultivating eukaryotic cell cultures and already contains minerals (Ca, Fe, K, Mg, Na in a variety of forms), carbohydrates (L-glucose, sodium pyruvate) and seven different vitamins that are important for eukaryotic cells in addition to the desired amino acids. In experiments, however, it has proved expedient for the cultivation of microbes to add further minerals (for some bacteria, NaCl in larger quantities, but in particular $Fe(II)SO_4$), glucose and vitamins in order to achieve better microbial growth. Finally, the isotopically labeled amino acids, which preferably should not already be present in unlabeled form, must be added. The media which are optimized for microbial growth can be produced, especially in freeze-dried form, in suitable package sizes and offered commercially for use in mass spectrometric determinations of resistances.

The media with added antibiotics can also be similarly prepared and offered commercially.

The invention claimed is:

1. A method of analyzing the resistance or susceptibility of microbes from a sample under investigation to an antibiotic, the method comprising:
    providing a synthetic growth medium which contains proteinogenic amino acids, wherein at least one of the amino acids is isotopically labeled, and wherein all of the isotopically labeled amino acids are labeled with isotopes from the group consisting of carbon, nitrogen, oxygen and sulfur and have the same integer mass difference $\Delta m$ in relation to corresponding unlabeled amino acids;
    cultivating said microbes in a first culture using the synthetic growth medium with the addition of the antibiotic;
    cultivating said microbes in a second culture using the synthetic growth medium without the addition of said antibiotic; and
    acquiring mass spectra of the microbes from the first and second cultures and comparing them to each other to determine an extent of a mass shift by said integer mass difference in the spectrum of the first culture.

2. A method according to claim 1, wherein only one amino acid is isotopically labeled and that amino acid amounts to less than five percent in ribosomal proteins of the microbes.

3. A method according to claim 1, wherein several amino acids are isotopically labeled and those isotopically labeled amino acids amount to less than ten percent overall in ribosomal proteins of the microbes.

4. A method according to claim 1 wherein, in comparing said mass spectra, (a) intensity ratios or differences of shifted and unshifted peaks of the same proteins in each case are calculated and/or (b) intensity ratios or differences of shifted and unshifted peaks of the same proteins in each case are averaged.

5. A method according to claim 1, wherein the synthetic medium contains substantially none of an unlabeled amino acid corresponding to an isotopically labeled amino acid.

6. A method of analyinq the resistance or susceptibility of microbes to an antibiotic, comprising the steps of:
    (a) cultivating the microbes in a synthetic medium in which at least one amino acid is isotopically labeled and all isotopically labeled amino acids are labeled with isotopes from the group consisting of carbon, nitrogen, oxygen and sulfur and have the same integer mass difference Lm in relation to corresponding unlabeled amino acids,
    (b) further cultivating microbes cultivated in step (a) in a first culture using a medium without isotopically labeled nutrient components and with the addition of the antibiotic;
    (c) further cultivating microbes cultivated in step (a) in a second culture using a medium without isotopically labeled nutrient components and without the addition of said antibiotic; and
    (d) acquiring mass spectra of the microbes from the first and second cultures and comparing them to each other to determine an extent of a mass shift by said integer mass difference in the spectrum of the first culture.

7. A method according to claim 6, wherein in step (a) only one amino acid is isotopically labeled and that amino acid amounts to less than five percent in ribosomal proteins of the microbes.

8. A method according to claim 6, wherein in step (a) several amino acids are isotopically labeled and those isotope-labeled amino acids amount to less than ten percent overall in ribosomal proteins of the microbes.

9. A method according to claim 6, wherein step (b) further comprises performing a plurality of cultivations of microbes cultivated in step (a) with the medium without isotopically labeled nutrient components, each of said plurality of cultivations comprising the addition of a different type of antibiotic or a different concentration of an antibiotic.

10. A method according to claim 6 wherein, in comparing said mass spectra (a) intensity ratios or differences of shifted and unshifted peaks of the same proteins in each case are calculated and/or (b) the intensity ratios or differences of shifted and unshifted peaks of the same proteins in each case are averaged.

11. A method according to claim 6 wherein the synthetic medium contains substantially none of an unlabeled amino acid corresponding to an isotopically labeled amino acid.

12. A method according to claim 1, wherein the synthetic medium is Eagle's minimal essential medium (EMEM) or Dulbecco's modified Eagle's medium (DMEM), in which at least one amino acid has been replaced by a corresponding isotopically labeled amino acid.

13. A method according to claim 12, wherein the synthetic medium has a NaCl concentration of more than 6.4 g/l.

14. A method according to claim 13, wherein the synthetic medium contains Fe(II)SO$_4$.

15. A method according to claim 6, wherein the synthetic medium is Eagle's minimal essential medium (EMEM) or Dulbecco's modified Eagle's medium (DMEM), in which at least one amino acid has been replaced by a corresponding isotopically labeled amino acid.

16. A method according to claim 15, wherein the synthetic medium has a NaCl concentration of more than 6.4 g/l.

17. A method according to claim 16, wherein the synthetic medium contains Fe(II)SO$_4$.

18. A method of analyzing the resistance or susceptibility of microbes from a sample under investigation to an antibiotic, the method comprising:
  providing a synthetic growth medium which contains proteinogenic amino acids, wherein at least one of the amino acids is isotopically labeled, and wherein all of the isotopically labeled amino acids are labeled with isotopes from the group consisting of carbon, nitrogen, oxygen and sulfur and have the same integer mass difference Δm in relation to corresponding unlabeled amino acids;
  cultivating said microbes in a first culture using the synthetic growth medium with the addition of the antibiotic;
  cultivating said microbes in a second culture using the synthetic growth medium without the addition of said antibiotic;
  cultivating said microbes in a third culture using a synthetic growth medium with unlabeled amino acids and without the addition of said antibiotic;
  acquiring mass spectra of the microbes from the cultures and comparing the mass spectrum of the first culture to the mass spectrum of the second culture and comparing the mass spectrum of the first culture to the mass spectrum of the third culture to determine an extent of a mass shift by said integer mass difference in the spectrum of the first culture.

19. A method of analyzing the resistance or susceptibility of microbes to an antibiotic, comprising the steps of:
  (a) cultivating the microbes in a synthetic medium in which at least one amino acid is isotopically labeled and all isotopically labeled amino acids are labeled with isotopes from the group consisting of carbon, nitrogen, oxygen and sulfur and have the same integer mass difference Δm in relation to corresponding unlabeled amino acids;
  (b) further cultivating microbes cultivated in step (a) in a first culture using a medium without isotopically labeled nutrient components and with the addition of the antibiotic;
  (c) further cultivating microbes cultivated in step (a) in a second culture using a medium without isotopically labeled nutrient components and without the addition of said antibiotic;
  (d) acquiring mass spectra of the microbes from the first and second cultures and acquiring a third mass spectrum from the microbes cultivated in step (a); and
  (e) comparing the mass spectrum of the first culture to the mass spectrum of the second culture and comparing the mass spectrum of the first culture to the third mass spectrum to determine an extent of a mass shift by said integer mass difference in the spectrum of the first culture.

\* \* \* \* \*